(12) United States Patent
Jagesar

(10) Patent No.: US 9,732,370 B2
(45) Date of Patent: Aug. 15, 2017

(54) METHOD FOR THE DETERMINATION OF THE PRESENCE OF AN ANTIBIOTIC IN A FLUID

(71) Applicant: DSM IP ASSETS B.V., Heerlen (NL)

(72) Inventor: Dhiredj Chandre Jagesar, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/787,859

(22) PCT Filed: Apr. 30, 2014

(86) PCT No.: PCT/EP2014/058778
§ 371 (c)(1),
(2) Date: Oct. 29, 2015

(87) PCT Pub. No.: WO2014/177597
PCT Pub. Date: Nov. 6, 2014

(65) Prior Publication Data
US 2016/0076071 A1    Mar. 17, 2016

(30) Foreign Application Priority Data
May 2, 2013 (EP) ..................................... 13166187

(51) Int. Cl.
*C12Q 1/18* (2006.01)
*A01N 47/44* (2006.01)

(52) U.S. Cl.
CPC ............... *C12Q 1/18* (2013.01); *A01N 47/44* (2013.01); *G01N 2400/00* (2013.01)

(58) Field of Classification Search
None
See application file for complete search history.

(56) References Cited

U.S. PATENT DOCUMENTS

2007/0092929 A1* 4/2007 Dekker .................... C12Q 1/18
435/32

FOREIGN PATENT DOCUMENTS

| EP | 0005891 A1 | 12/1979 |
| EP | 0285792 A1 | 10/1988 |
| EP | 0611001 A1 | 8/1994 |
| EP | 1639122 A1 | 3/2006 |
| WO | 2005005655 A1 | 1/2005 |
| WO | 2013057182 A1 | 4/2013 |

OTHER PUBLICATIONS

International Search Report from corresponding PCT/EP2014/058778, mailed Jul. 23, 2014.
Gilbertson et al., "Modified Microbiological Method for the Screening of Antibiotics in Milk", 1995, J. Dairy Sci, vol. 78, XP27050235, pp. 1032-1038.

* cited by examiner

*Primary Examiner* — Kade Ariani
(74) *Attorney, Agent, or Firm* — McBee Moore Woodward & Vanik IP, LLC; Susan McBee; Chester Moore

(57) ABSTRACT

The present invention provides a method and test for the determination of the presence or absence of an antibiotic in a sample such as milk.

9 Claims, No Drawings

METHOD FOR THE DETERMINATION OF THE PRESENCE OF AN ANTIBIOTIC IN A FLUID

CROSS REFERENCE TO RELATED APPLICATIONS

This application is a §371 National Stage Application of PCT/EP2014/058778, filed 30 Apr. 2014, which claims priority to EP 13166187.8, filed 2 May 2013.

BACKGROUND

Field of the Invention

The present invention relates to a new and improved microbial growth inhibition test for the determination of the presence or absence of an antibiotic in a sample such as milk.

Description of Related Art

Nowadays, antibiotics are frequently used in veterinary practice not only for treatment of bacterial infections, but also for prophylactic purposes to improve the productivity of foodstuffs. In recent years, this irresponsible misuse of antibiotics as a preventive measure has been a decisive factor favoring the growth of bacterial resistance.

Antibiotic residues are known to be among the most frequently detected contaminants in milk and dairy products and cause important problems in this industrial sector at economical level.

To prevent the negative impact of antibiotic residues on human health and on the entire ecosystem, maximum residue limits (MRLs) for antimicrobials in foodstuff of animal origin have been established by various legislators (such as the EU). The MRL is the maximum concentration of residues of a pharmacologically active substance which may be permitted in food or animal origin.

Microbial growth inhibition tests have been developed for the determination of the presence or absence of antibiotic residues in a sample. Examples of such tests have been described in for example EP 0 005 891A and EP 0 285 792A. The tests described therein are ready-to-use tests that make use of a test organism and an indicator molecule, for instance a pH- and/or redox-indicator. The general principle of the test is that, when an antibiotic is present in a sample in a concentration sufficient to inhibit growth of the test organism, the color of the indicator will stay the same, while, when no inhibition occurs, growth of the test organism is accompanied by the formation of acid or reduced metabolites or other phenomena that will induce an indicator signal.

In general a microbial growth inhibition test has to comply with the basic legislative specifications and reliably identify the presence of antimicrobial residues in the examined samples in concentrations equal to the MRLs. However, microbial growth inhibition tests exist that are unable to detect some antimicrobial residues at their respective MRLs, i.e. they have a limited sensitivity for certain antibiotics. In particular, currently commercialized microbial growth inhibition tests have a limited sensitivity for aminoglycoside antibiotics.

In EP 1 639 122A it has been described that the sensitivity of a microbial growth inhibition test can be increased by using the indicator bromothymol blue. However, the use of this indicator predominantly changes the sensitivity of a microbial growth inhibition test for beta-lactam antibiotics.

In view thereof, there is still a need for a microbial growth inhibition test with an increased sensitivity for, for instance, aminoglycoside antibiotics.

SUMMARY

It is an object of the present invention to provide a simple, inexpensive and easy-to-use, broadly applicable microbial growth inhibition test for the determination of the presence or absence of an antibiotic in a sample such as milk. Surprisingly, it has been found that the sensitivity of a microbial growth inhibition test for aminoglycoside antibiotics can be increased when an aminoglycoside antibiotic such as streptomycin is added to the test.

DETAILED DESCRIPTION OF A PREFERRED EMBODIMENT

In a first aspect the present invention is directed to a method for detecting the presence of an antibiotic in a sample, the method comprising the steps of (a) contacting the sample with a microbial growth inhibition test, said test comprising at least a test organism, an indicator and an aminoglycoside antibiotic, (b) growing the test organism, and (c) detecting the amount of growth of the test organism, wherein lack of growth reflects the presence of an antibiotic in the sample.

Optionally, the method comprises the step of preparing the test organism before the test organism is contacted with the sample. Therefore, the present invention is also directed to a method for detecting the presence or absence of an antibiotic in a sample, the method comprising the steps of (a) preparing a test organism, (b) contacting the sample with a microbial growth inhibition test, said test comprising at least the test organism, an indicator and an aminoglycoside antibiotic, (c) growing the test organism, and (d) detecting the amount of growth of the test organism, wherein lack of growth reflects the presence of an antibiotic in the sample.

In a further aspect the invention relates to the use of an aminoglycoside antibiotic to increase the sensitivity of a microbial growth inhibition test for the determination of the presence of an antibiotic in a sample. In an embodiment the antibiotic in the sample is an aminoglycoside antibiotic.

In a further aspect the invention relates to a closed packaging comprising at least one microbial growth inhibition test, said test comprising at least a test organism, an indicator and an aminoglycoside antibiotic.

In another aspect the invention is concerned with a kit comprising an aminoglycoside antibiotic and a microbial growth inhibition test, said test comprising at least a test organism and an indicator.

The below embodiments are applicable to all aspects of the invention.

In an embodiment of the invention the aminoglycoside antibiotic is added to the test before the test organism is grown, i.e. before the test is started. It can also be added after the start of the test, but this is less preferred. In an embodiment the aminoglycoside antibiotic is added to the sample. This can be done before, during or after the sample is contacted with the test. In a preferred embodiment the aminoglycoside antibiotic is added to the test, i.e. it is part of the test medium. Preferably, the aminoglycoside antibiotic is present in the test, i.e. in the test medium, before the test is contacted with the sample. In other words, the microbial growth inhibition test comprises the aminoglycoside antibiotic in the absence of sample. In yet other words, the test medium of the microbial growth inhibition test comprises the aminoglycoside antibiotic before the sample is added to the test medium.

The test is able to determine the presence of an antibiotic in a sample. The antibiotic to be determined can be an antibiotic from a family of antibiotics that is selected from the group consisting of the family of beta-lactam antibiotics, the family of tetracycline antibiotics, the family of sulfonamide antibiotics, the family of aminoglycoside antibiotics, the family of macrolide antibiotics, the family of lincosamides, and the family of quinolone antibiotics. However, the test can also be used to detect other than the above-mentioned antibiotics.

Due to the presence of an aminoglycoside antibiotic in the test, the sensitivity of the test for aminoglycoside antibiotics such as streptomycin and dihydrostreptomycin increases. Surprisingly, it was found that the presence of an aminoglycoside antibiotic in the test had no effect on the sensitivity of the test for other antibiotic classes such as beta-lactams (e.g. penicillin G) and tetracyclines (e.g. oxytetracycline). The presence of an aminoglycoside antibiotic in the test thus specifically increases the sensitivity of the test for aminoglycoside antibiotics.

In an embodiment the aminoglycoside antibiotic is selected from the group consisting of streptomycin, dihydrostreptomycin, amikacin, apramycin, arbekacin, astromicin, bekanamycin, dibekacin, framycetin, gentamicin, hygromycin B, isepamicin, kanamycin, neomycin, netilmicin, paromomycin, rhodostreptomycin, ribostamycin, sisomycin, spectinomycin, tobramycin, and verdamicin. The term "aminoglycoside antibiotic" also includes mixtures of two or more different aminoglycoside antibiotics. For instance, any combination of two or more antibiotics of the above-mentioned group can be used. In a preferred embodiment the aminoglycoside antibiotic used in the various aspects of the present invention is selected from the group consisting of streptomycin and dihydrostreptomycin.

In an embodiment the concentration of the aminoglycoside antibiotic is between 10 ppb and 10,000 ppb, preferably between 100 ppb and 10,000 ppb and more preferably between 500 ppb and 5,000 ppb. For clarification purposes only, the mentioned concentration ranges relate to the concentration of aminoglycoside antibiotic in the test in the absence of sample.

In an embodiment the microbial growth inhibition test comprises an indicator. In other words, the indicator is present in the test medium. The term "indicator" refers to a substance used to measure (for example by change of colour or fluorescence) the condition of a test medium with respect to the presence of a particular component (for example an acid, a base, oxidizing or reducing agents). Particularly useful are indicators that, upon changing from one state to the other, provide a visually detectable signal such as a change in color or fluorescence. The amount of indicator in the test medium is generally between 0.01 and 50 g/l test medium, preferably between 0.1 and 10 g/l, more preferably between 0.5 and 5 g/l, most preferably between 1 and 3 g/l. The indicator may be a pH-indicator, a redox-indicator or a combination thereof. The term also may refer to two or more indicators. The skilled artisan will appreciate that many indicators are suitable for the purpose of the present invention. Examples of suitable indicators can be found in handbook H. J. Conn's Biological Stains, R. D. Lillie ed., Baltimore, 1969.

The test may have the form of a liquid, a solid or a gel-like matrix. In an embodiment of the invention the microbial growth inhibition test further comprises a gelling agent. The term "gelling agent" as used herein refers to a compound that assists in changing a mixture into a gel or taking on the form of a gel. Examples of suitable gelling agents in the various aspects of the present invention include, but are not limited to, agar, gelatin, alginic acid and salts thereof, carrageenan, locust bean gum (Carob gum), hydroxypropyl guar and derivatives thereof, processed eucheuma seaweed and the like. Agar is the preferred gelling agent. In an embodiment a test organism and an indicator and optionally other additional ingredients such as the aminoglycoside antibiotic are introduced into an agar solution. The agar solution is allowed to solidify to form the test medium such that the test organism stays alive, but cannot multiply because of e.g. low temperature. In general, the gelling agent will constitute a large part of the test medium. The amount of gelling agent in the test is generally between 1 and 200 g/l test medium, preferably between 2 and 50 g/l, more preferably between 5 and 20 g/l, most preferably between 7 and 15 g/l.

When the test medium has the form of a solid matrix, it may comprise a carrier material such as a ceramic, cotton, glass, a metal particle, a polymer in any shape or form, a silicate, a sponge, wool and the like. Alternatively, the test may have the form of a tablet, disc or paper filter comprising the test organism, indicator and optionally nutrient. The three constituents may be present in a single tablet, but also in two or more tablets. Of course, test systems combining test media in solid, liquid and/or gel-like form may be used.

Optionally, the microbial growth inhibition test may also contain nutrients, stabilizers, salts, buffers and/or viscosity-increasing agents. The term "nutrient" as used herein refers to a nutritive substance or ingredient that promotes and/or is required for the growth of the test organism. Suitable nutrients depend from the microorganism used in the test system. The test medium may comprise two or more different nutrients. They include, but are not limited to, assimilable carbon sources such as carbohydrates such as e.g. glucose, fructose, sucrose, lactose and dextrose; assimilable nitrogen sources such as amino acids such as e.g. peptone or tryptone; sources of vitamins and growth factors such as beef or yeast extract; and sources of minerals such as earth alkaline metal salts such as salts of e.g. barium or calcium. Suitable additional ingredients that may be present in the test according to the present invention are known to the person skilled in the art and include, but are not limited to, other agents (other than an aminoglycoside antibiotic) that increase or decrease the sensitivity of the test for antibiotics.

In an embodiment of the invention the test organism is selected from the group consisting of a *Bacillus* species, an *Escherichia* species and a *Streptococcus* species. "Test organism" as used herein also includes spores, e.g. spores of any of these species. In a preferred embodiment of the invention the test organism is thermophilic. Examples are *Bacillus stearothermophilus* or *Streptococcus thermophilus*, with *Bacillus stearothermophilus* being preferred. These species may be introduced in the test as units capable of producing colonies, or Colony Forming Units (CFUs). The term "CFU" as used herein refers to the number of test organisms, spores of test organisms, partially germinated spores of test organisms, vegetative cells or any mixture thereof capable of producing colonies of organisms. The concentration of said CFUs is expressed as Colony Forming Units per ml of test medium (CFU/ml) and is usually in the range of $1 \times 10^5$ to $1 \times 10^{12}$ CFU/ml, preferably $1 \times 10^6$ to $1 \times 10^{10}$ CFU/ml, more preferably $2 \times 10^6$ to $1 \times 10^9$ CFU/ml, most preferably $5 \times 10^6$ to $1 \times 10^8$ CFU/ml, or still more preferably $5 \times 10^6$ to $2 \times 10^7$ CFU/ml.

In an embodiment of the invention the sample may be derived from a body liquid, an organ, meat or eggs. Antibiotics might also be present in food products in which these animal products are added as an ingredient. Examples of food products are milk, processed milk products (e.g. cream, yoghurt); meat of cow, pig, poultry and fish; sea food such as shrimps; liver; processed meat products such as sausages; ready-to-eat meals and baby food. Antibiotics might also be present in body liquids or animal tissues, which are suitable for examination by for example food inspection authorities. Examples are blood, kidney tissue or pre-urine obtained from the kidney and urine. Urine and blood are suitable for examination prior to slaughtering of the animal. Antibiotics may also be present in waste water, water from any type industry, etc. In a preferred embodiment the sample is urine, blood, egg, honey, kidney, meat, liver, fish, shrimp, feed and/or milk, with milk being most preferred. The milk can be derived from cows, but also from sheep, goats, yaks, water buffalo, horses, reindeers and camels. In a preferred embodiment the sample is a fluid sample. In an embodiment the sample might not be fluid and fluid comprising the antibiotic(s) needs to be extracted from the sample.

Preferably, there is minimal or no germination and outgrowth of the test organism prior to the addition of fluid sample. This is achieved by storing and keeping the test under conditions comprising an unfavorable temperature and/or an unfavorable pH-value and/or the absence of nutrients essential for germination and outgrowth of the test organism. Of course, the conditions should not cause irreversible damage to all CFUs present in the microbial growth inhibition test.

After contacting the sample with the test organism, growth of the test organism is allowed to take place during a period sufficiently long for the test organisms to grow in case no antibiotic is present. The period can be determined by including a control sample, i.e. a sample that is antibiotic free, and end the incubation of all samples tested, when the test measuring the control sample has switched color. It can also be decided to incubate all samples for a fixed period of time. Growth is induced by adding nutrients, optionally before the contacting of said sample, and/or raising the temperature, and/or providing for a pH-value at which the test organism is able to grow. Alternatively, these conditions may be established prior to contact of the fluid sample with the test organism. For instance, growth of the test organism may take place when the test organism is incubated at a temperature conducive to growth of the test organism.

The amount of growth of the test organism is detected by observing a change of an indicator. Lack of growth reflects the presence of an antibiotic in the sample, whereas growth reflects the absence of an antibiotic in a sample. As indicated above, the presence of an antibiotic is determined by a change of the indicator(s) used. Usually, when an antibiotic is present in a sample, there is no change in indicator. When no antibiotic is present in a sample, microbial growth will occur resulting in a change of indicator. When, for example such a change is a color change, said color change may be observed visually. However, said color change may also be determined using an arrangement that generates digital image data or an arrangement that generates analog image data and converts said analog image data into digital image data followed by interpretation of said digital image data by a computer processor. An example of such an arrangement, i.e. a sample-reading device such as a scanner coupled to a personal computer, is described in WO 03/033728. Another example of such an arrangement, i.e. a combined sample incubating and sample-reading device (such as a scanner combined with an incubator) coupled to a personal computer is described in WO 2007/090683. Both documents are herewith incorporated by reference.

Optionally, certain test ingredients are sterilized and usually the pH of the test is adjusted to the required value. Optionally, samples may be mixed (e.g. with other samples, but also with salts, buffering compounds, nutrients, stabilizers, enzymes, and the like), concentrated and/or diluted (e.g. with diluting liquids such as water, solvents, and the like) prior to addition to the test organism.

In an embodiment of the invention, the test organism is grown by incubating it for a predetermined period, preferably within a time span of 0.5 to 6 hours, more preferably between 0.75 to 5 hours, most preferably between 1.0 to 4 hours and in particular between 2 and 3.5 hours. Preferably the test organism is incubated at a predetermined temperature, preferably the optimal growth temperature of the test organism. When, for example, thermophilic test organisms are used, said temperature is preferably between 40 and 70° C., more preferably between 50 and 65° C., most preferably between 60 and 64° C. Optionally said reaction can be carried out with the aid of a thermostatic device. Alternatively, the time required for growth of the test organism is equal to the time that is required for a calibration sample with a known amount of antibiotic to induce a change in the indicator or the time that is required for a control sample with no antibiotic to induce a change in the indicator.

In an embodiment of the invention at least one microbial growth inhibition test is present in a packaging. The test comprises at least a test organism, an indicator and an aminoglycoside antibiotic. In a preferred embodiment the packaging is closed. "Closed" as used herein means that the test(s) that are present within the packaging have not been into contact with a sample yet. The packaging can be a box or any other suitable packaging unit. It can be made of any material suitable for making packaging units. Preferably, the packaging comprises more than one microbial growth inhibition test. The microbial growth inhibition test may be present in a container. The container may have any shape and size and can be from any material available, provided that observation of indicator changes is possible. The container may be a tube (e.g. an ampoule), but may also be a well such as a well that is part of a plate, e.g. a microtitre plate, i.e. a flat plate with multiple wells. The closed packaging may for instance comprise 5 plates, 10 plates, or 20 plates and/or 25 tubes or 100 tubes.

The packaging may further comprise a sampling device. A sampling device is a device with the aid of which fluid can be added to the microbial growth inhibition test. Examples include, but are not limited to, a syringe, a pipette or an automated pipetting system. Such a syringe or pipette may be designed in such a fashion that with only one mode of operation a predetermined volume can be withdrawn from the fluid sample to be analyzed. Optionally, systems known in the art with which more than one syringe or pipette can be operated with one single handling may be applied. Optionally, the packaging further comprises means for sealing of the containers after sample has been added to the containers and/or during incubation of the containers. In addition, the packaging may comprise an insert with instructions for use and/or a means for setting the time needed for incubation.

The invention also pertains to a kit comprising (a) an aminoglycoside antibiotic, and (b) a microbial growth inhibition test. As indicated above, the test may be present in a container. The aminoglycoside antibiotic may also be present in a container. The aminoglycoside antibiotic can be added to the test shortly before the test is used.

Optionally, the ratio of the sample to test medium exceeds 2:3 (0.68:1) (v/v). Preferably, said ratio is at least 20:27 (0.74:1) (v/v), more preferably said ratio is at least 25:27 (0.93:1) (v/v); most preferably said ratio is at least 2:1 (v/v). It has been found that there is no technical reason for an upper limit to the amount of sample. In practice, this volume should not exceed the maximum content of the container that holds the test medium. For example, in a 2 ml container having 0.2 ml test medium, no more than 1.8 ml of fluid sample should be added. In practice, containers for performing the method of the present invention have a volume that rarely exceeds 50 ml and hence the amount of fluid sample to be added shall not exceed 50 ml, preferably 10 ml, more preferably 5 ml, still more preferably 2 ml, most preferably 1 ml. Thus, in general, the upper limit of the ratio of the volume of fluid sample to the volume of test medium is 250:1 (v/v), preferably 50:1 (v/v), more preferably 25:1 (v/v), still more preferably 10:1 (v/v), most preferably 5:1 (v/v). In a preferred embodiment the volume of the dilution/sample is greater than the volume of test medium.

Optionally, the packaging may further comprise a thermostatic device, with the aid of which samples can be kept at a pre-set temperature, such as the temperature at which the test organism shows sufficient growth. Preferably, said thermostatic device is designed in such a fashion that it can hold the containers. Optionally, the thermostatic device is coupled to a means for setting the time needed for incubation such that heating and/or cooling is stopped after lapse of a pre-set period.

Optionally, the packaging further comprises a data carrier loaded with a computer program suitable for instructing a computer to analyze digital data obtained from a sample-reading device. Said data carrier may be any carrier suitable for storing digital information such as a CD-ROM, a diskette, a DVD, a memory stick, a magnetic tape or the like. Advantageously, said data carrier loaded with a computer program provides for easy access to the latest available computer programs suitable for use in the method of the present invention.

EXAMPLES

Example 1

Effect of an Aminoglycoside Antibiotic in the Test Medium on the Detection Limit of Aminoglycoside Antibiotics in a Microbial Growth Inhibition Test In order to establish the effect of an aminoglycoside antibiotic on the sensitivity of a microbial growth inhibition test for aminoglycoside antibiotics, the following series of experiments was carried out.

As a reference, a commercially available test system without any added aminoglycoside antibiotic (DSM Delvotest® SP-NT, plates containing 8×12 test wells) was used. In addition, two different test systems were prepared by modifying the reference test by adding the aminoglycoside antibiotic streptomycin to the test medium in a final concentration of 100 ppb or 1000 ppb.

The detection limits of four different antibiotics were measured in the reference test and in the tests with modified medium containing different concentrations of streptomycin. The antibiotics that were measured were streptomycin and dihydrostreptomycin (DH-streptomycin) (both belonging to the aminoglycoside antibiotic family), penicillin G (belonging to the beta-lactam antibiotic family), and oxytetracycline (belonging to the tetracycline antibiotic family) Five different concentrations of each antibiotic (see Table 1) were measured. Hundred microliter antibiotic-free milk or hundred microliter milk spiked with the respective concentrations of antibiotic was added to the test medium (170 μl) and incubated at 64° C. in a water bath.

The tests were visually determined at the point in time where a sample without antibiotic had changed colour from purple to yellow. At this point, the plates were cooled in an ice bath for 5 minutes. The cooled plates were scanned on a Delvo® scanner. The colour of each well was expressed as a Z-value; a purple colour gives rise to a positive Z-value, while a yellow colour has a negative Z-value. The Z-value of test results with samples without antibiotic is typically $-5<Z<-10$. Detailed description of the scanning technology and the expression of the colour in Z-values are described in WO 03/033728.

For the determination of the detection limit for each antibiotic, a dose-response function (Z-value versus concentration of antibiotic) was constructed. The detection limit is defined as the antibiotic concentration where the S-shaped dose-response function has a Z-value equal to the cut-off value. For Delvotest® SP-NT a cut-off Z-value of 0 was used. The calculated detection limits are summarized in Table 2.

The results clearly show that addition of an aminoglycoside antibiotic to the test medium results in a test system having a strongly increased sensitivity for aminoglycoside antibiotics, while the sensitivity for beta-lactam antibiotics and tetracycline antibiotics remains unaffected.

TABLE 1

Antibiotic concentration of the spiked milk samples.

| Streptomycin (in ppb) | DH-streptomycin (in ppb) | Penicillin G (in ppb) | Oxytetracycline (in ppb) |
| --- | --- | --- | --- |
| 0 | 0 | 0 | 0 |
| 100 | 100 | 0.3 | 50 |
| 200 | 200 | 1.0 | 100 |
| 500 | 500 | 2.0 | 200 |
| 1000 | 1000 | 3.0 | 300 |
| 2500 | 2500 | 4.0 | 500 |

TABLE 2

Detection limit of different antibiotics in Delvotest ® SP-NT containing different concentrations of streptomycin.

| Streptomycin concentration in test (in ppb) | Detection limit (in ppb) | | | |
| --- | --- | --- | --- | --- |
| | Strepto-mycin | DH-strepto-mycin | Penicillin G | Oxytetra-cycline |
| 0 | 2005 | 1471 | 1.04 | 264 |
| 100 | 1186 | 982 | 0.95 | 239 |
| 1000 | 676 | 445 | 1.07 | 343 |

The invention claimed is:

1. method for detecting the presence of an antibiotic in a sample, the method comprising:
(a) contacting the sample with a microbial growth inhibition test, said test comprising at least a test medium, a test organism, an indicator and an aminoglycoside antibiotic,
(b) incubating the test after contacting the sample under conditions conducive to growth of the test organism, and (c) detecting the amount of growth of the test organism, wherein lack of growth reflects presence of an antibiotic in the sample, wherein the antibiotic in the sample is from a family of antibiotics selected from the group consisting of: the family of beta-lactam antibiotics, the family of tetracycline antibiotics, the family of sulfonamide antibiotics, the family of aminoglycoside antibiotics, the family of macrolide antibiotics, the family of lincosamides, and the family of quinolone antibiotics;

wherein the test medium of the microbial growth inhibition test comprises the aminoglycoside antibiotic before the sample is added to the test medium; and wherein lack of growth of the test organism is determined by lack of change in the indicator.

2. The method according to claim 1, wherein the aminoglycoside antibiotic in the test is selected from the group consisting of streptomycin, dihydrostreptomycin, amikacin, apramycin, arbekacin, astromicin, bekanamycin, dibekacin, framycetin, gentamicin, hygromycin B, isepamicin, kanamycin, neomycin, netilmicin, paromomycin, rhodostreptomycin, ribostamycin, sisomycin, spectinomycin, tobramycin, and verdamicin.

3. The method according to claim 1, wherein the indicator is a pH indicator and/or a redox indicator.

4. The method according to claim 1, wherein the test organism is selected from the group consisting of a *Bacillus* species, an *Escherichia* species and a *Streptococcus* species.

5. The method according to claim 1, wherein the sample is a fluid sample.

6. The method according to claim 5, wherein the sample is milk.

7. The method according to claim 1, wherein the test organism is thermophilic.

8. The method according to claim 1, wherein the test further comprises a gelling agent.

9. The method according to claim 1, wherein the concentration of the aminoglycoside antibiotic in the test is 10 ppb to 10,000 ppb.

* * * * *